United States Patent [19]

Pazemenas

[11] 4,444,546

[45] Apr. 24, 1984

[54] OCCLUSION DETECTION APPARATUS AND METHOD

[75] Inventor: Vytas V. Pazemenas, Sunnyvale, Calif.

[73] Assignee: Oximetrix, Inc., Mountain View, Calif.

[21] Appl. No.: 188,618

[22] Filed: Sep. 19, 1980

[51] Int. Cl.³ .............................................. A61M 5/00
[52] U.S. Cl. ...................................... 417/12; 417/18; 417/45; 417/63
[58] Field of Search ........... 128/214 R, 214 E, 214 F; 222/63, 637, 638, 639, 642, 643; 417/12, 18, 44, 45, 63

[56] References Cited

U.S. PATENT DOCUMENTS

| | | | |
|---|---|---|---|
| 3,985,133 | 12/1976 | Jenkins et al. | 128/214 F |
| 4,056,333 | 11/1977 | Lundquist | 417/63 |
| 4,137,913 | 2/1979 | Georgi | 128/214 F |
| 4,173,224 | 11/1979 | Marx et al. | 128/214 F |
| 4,191,184 | 4/1980 | Carlisle | 128/214 F |
| 4,207,031 | 6/1980 | Maskrey et al. | 417/12 |
| 4,210,138 | 7/1980 | Jess et al. | 128/214 F |
| 4,256,437 | 3/1981 | Brown | 417/45 |
| 4,277,226 | 7/1981 | Archibald | 417/63 |
| 4,299,218 | 11/1981 | Knigge et al. | 128/214 F |

OTHER PUBLICATIONS

"A Description of the Valleylab Intravenous and Intra-Arterial Fluid Delivery System".

Primary Examiner—Richard J. Apley
Assistant Examiner—George Yanulis
Attorney, Agent, or Firm—Lyon & Lyon

[57] ABSTRACT

An improved occlusion detection apparatus and method for use in a pumping apparatus wherein a motor control sequencer provides signals adapted to rotate the shaft of a motor and a pump mechanism through a pumping cycle. The motor is advantageouly initially operated at a first higher torque to insure proper starting of the pumping cycle and is subsequently operated at a second lower torque through the remainder of the pumping cycle, the motor stalling if an occlusion within a fluid delivery system causes the back pressure within the delivery system to exceed the torque capabilities of the motor. An occlusion detector times the pumping cycle and if the cycle exceeds a first predetermined time period, an occlusion alarm is generated. The occlusion detector may further cause the motor control sequencer to increase motor torque to attempt to complete the pumping cycle or may de-energize the motor after a second predetermined period to prevent damage to the pumping apparatus.

15 Claims, 5 Drawing Figures

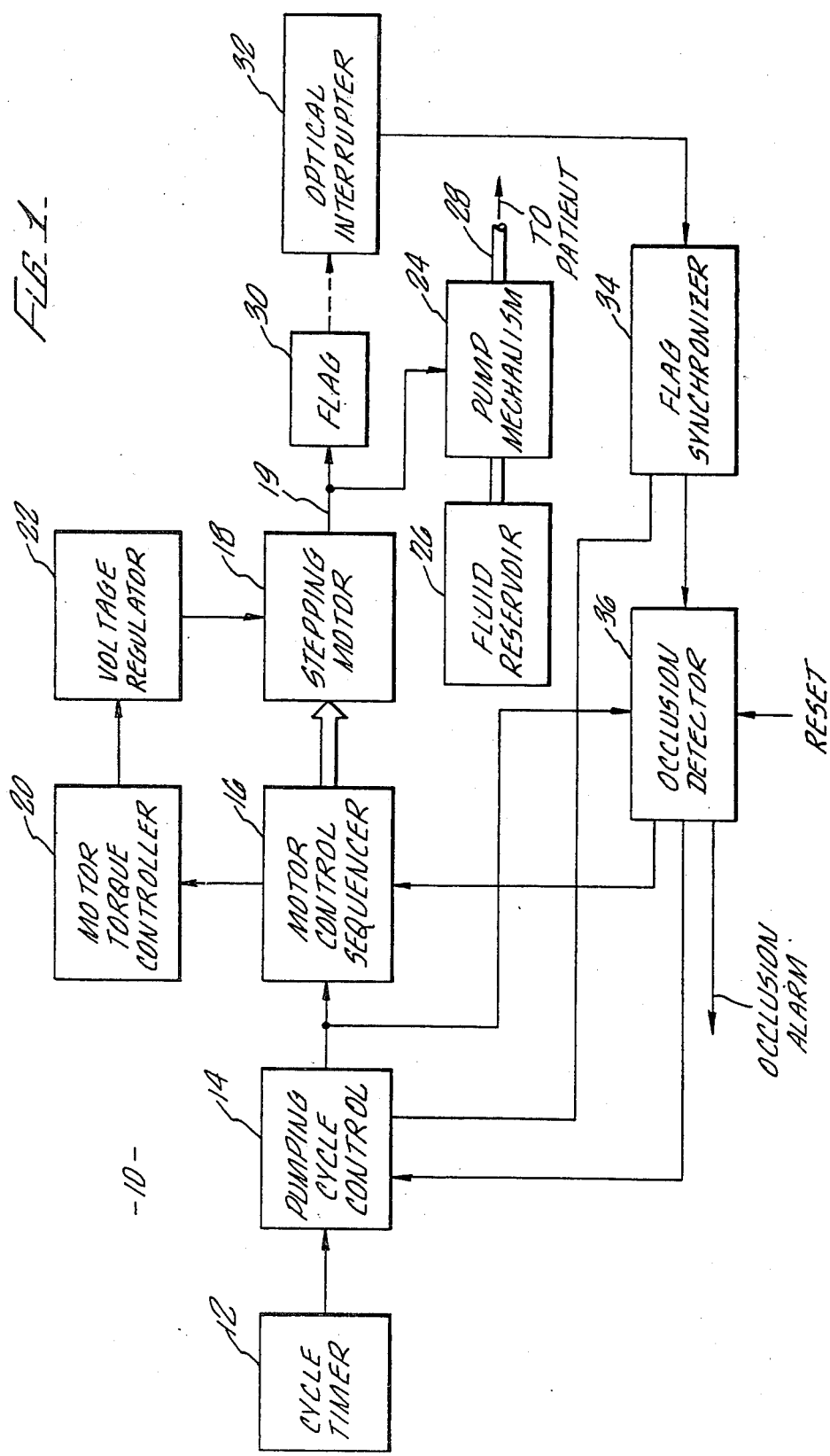

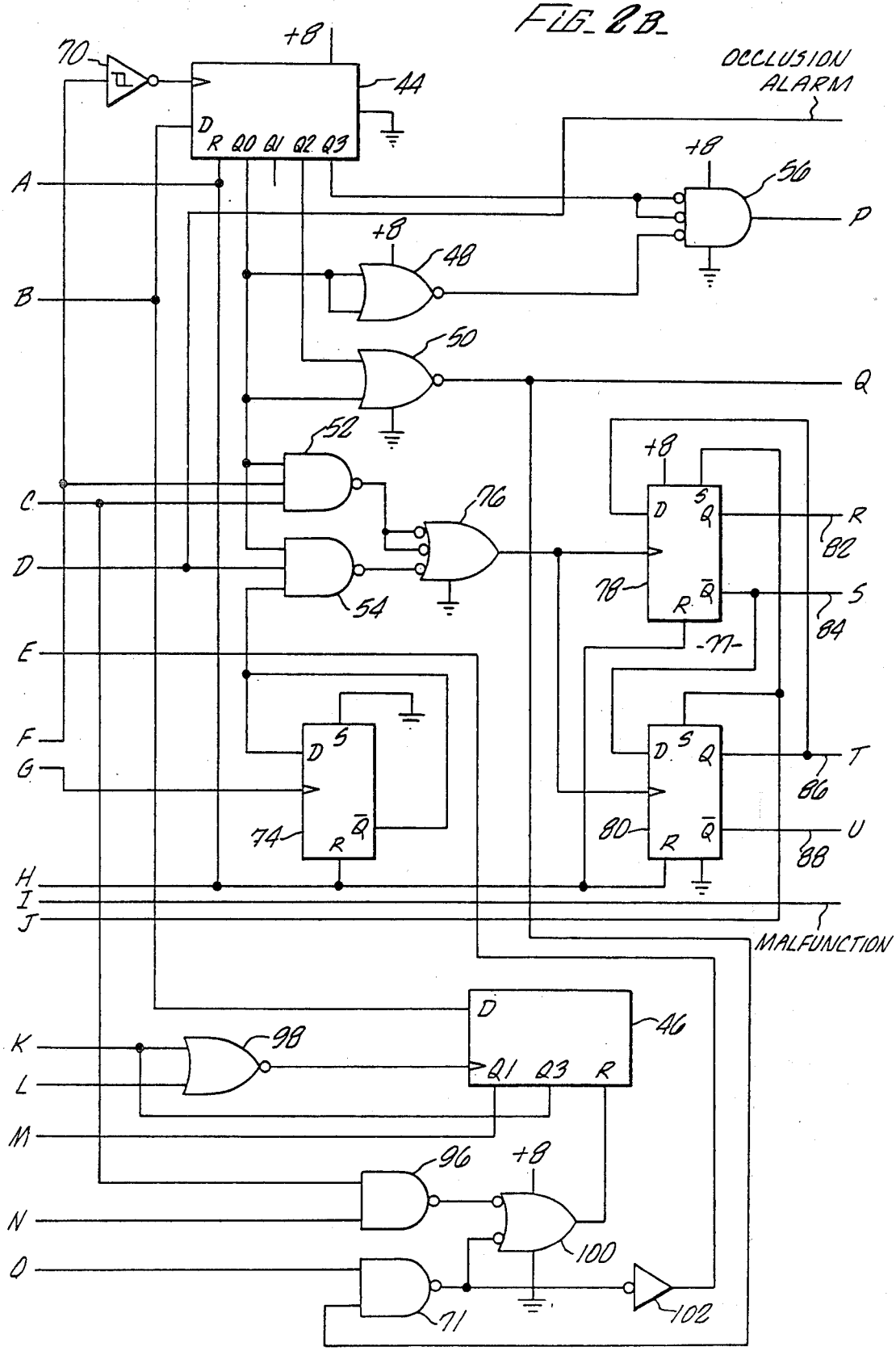
FIG_2B

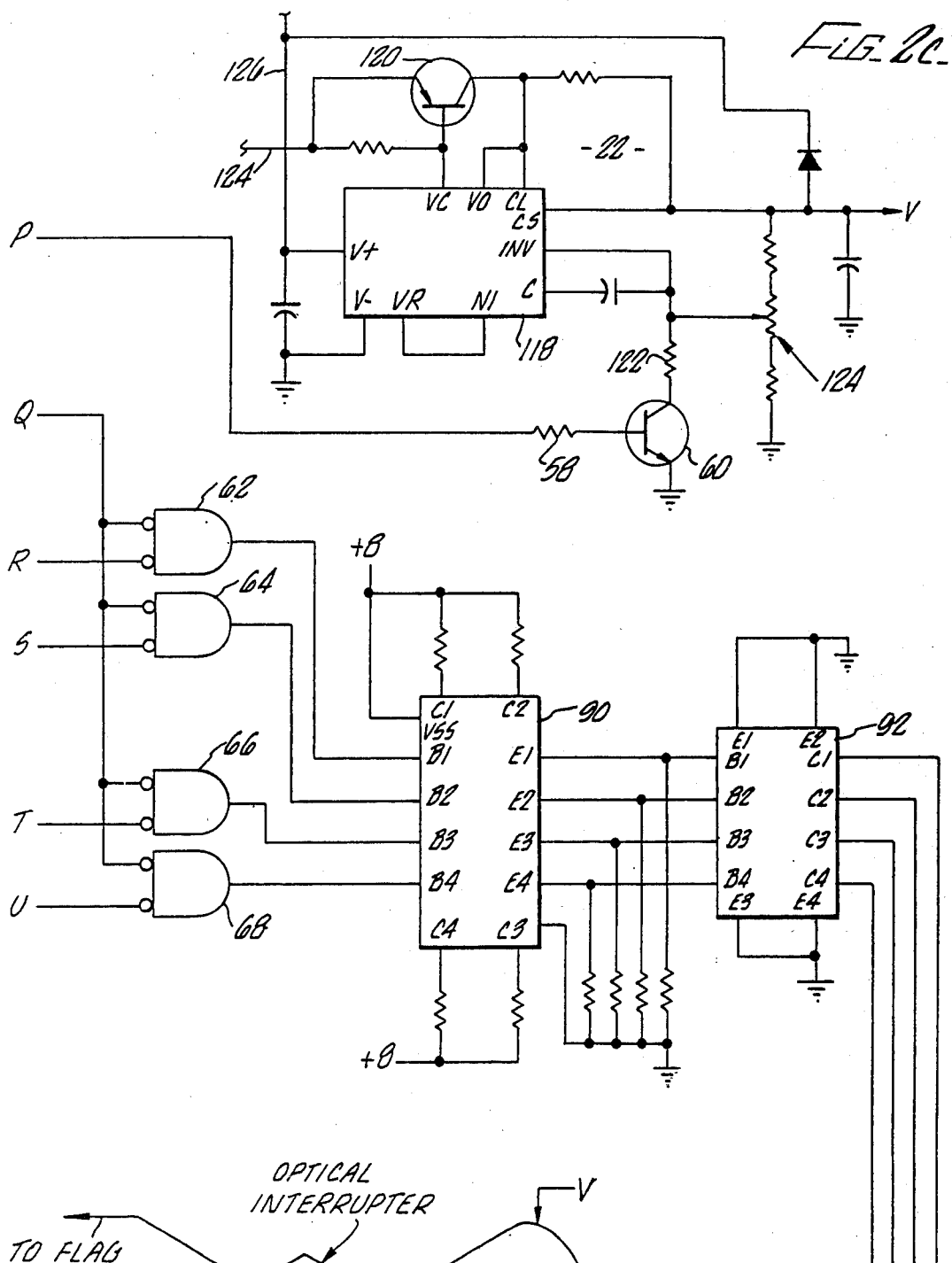
FIG. 2C.
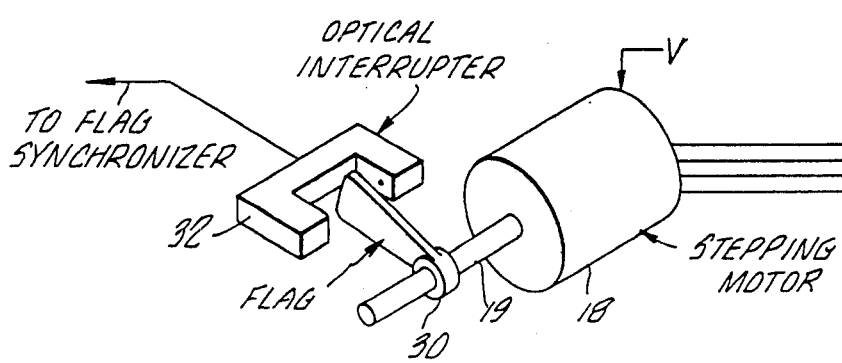

OCCLUSION DETECTION APPARATUS AND METHOD

BACKGROUND OF THE INVENTION

The present invention relates generally to infusion therapy pumping apparatus and more particularly to an improved occlusion detection apparatus and method therefore.

With intravenous infusion therapy pumping apparatus, it is desirable to detect occlusions within the fluid delivery system connecting the apparatus to a patient and to prevent pressure build-up within such a fluid delivery system. Various devices have been employed to this end.

For example, devices for limiting the pressure build-up within the fluid delivery system include devices which in some way utilize the relative stiffness of flexible tubing as an indication of pressure. In these system, however, it is often difficult to precisely control the pressure at which fluid delivery is reduced or stopped and this pressure may vary according to changes within the stiffness of the tubing resulting from, for example, temperature variations. Also, these systems are generally relatively complex.

Yet other systems may include a code wheel to monitor the rotation of a motor or a spring mechanism which yields when the pressure within the fluid delivery system exceeds a holding limit. These systems again are generally elaborate and expensive and, at least for the system employing the yield spring, may not be easily adjustable for various pressures.

SUMMARY OF THE INVENTION

The improved occlusion detection apparatus and method of the present invention overcomes the limitations and disadvantages set forth above. In an exemplary embodiment, an apparatus in accordance herewith includes a motor control sequencer which operates a motor and a pump mechanism actuated by the motor shaft through a pumping cycle. The motor is advantageously initially operated at a first higher torque to ensure proper starting of the motor and the motor torque is then decreased through the remainder of the pumping cycle. If an occlusion within the fluid delivery system coupled to the pump mechanism causes the pressure within the delivery system to exceed the torque capabilities of the motor, the motor stalls. An occlusion detector monitors the time period of the pumping cycle and, if a first predetermined length of time is exceeded, an occlusion alarm is provided. Moreover, the occlusion detector may control the motor control sequencer so as to again increase the torque developed by the stepping motor to attempt to complete the stalled pumping cycle. If the pumping cycle is not completed within a second predetermined period of time, the occlusion detector further controls the motor sequencer to de-energize the motor.

An exemplary method in accordance with the present invention may include energizing a motor to operate the motor at a first torque in response to a pumping cycle command, operating the motor at a second torque less than the first torque after a predetermined period and determining when the motor shaft is in a predetermined position to provide an indication thereof. The method may further include de-energizing the motor in response to the indication and detecting when the time period following the pumping cycle command exceeds a predetermined limit to thereby detect an occlusion in the fluid delivery means.

Thus, the apparatus and method of the present invention are desirably relatively simple and inexpensive to implement. The higher motor starting torque assures reliable starting of the motor while the lower second running torque can be substantially less than the starting torque to thereby detect relatively low partial or full occlusion pressures within the fluid delivery system. Furthermore, the second lower running torque of the motor accurately establishes the pressure within the fluid delivery system at which the motor stalls yet is easily and quickly adjustable to accordingly easily and quickly vary the pressure at which the motor stalls.

It is thus an object of the present invention to provide an improved occlusion detection method and apparatus.

It is a further object of the present inventon to provide an improved occlusion detection apparatus and method employing a motor operated at a first torque for starting and at a second torque for occlusion detection.

IN THE DRAWINGS

These and other objects and advantages of the present invention are apparent from the entire specification and from the following detailed description in conjunction with the drawings in which:

FIG. 1 is a block diagram of an improved occlusion detection apparatus in accordance with the present invention;

FIG. 2 comprising FIGS. 2A-2C are schematic diagrams of portions of the block diagram of FIG. 1.

DETAILED DESCRIPTION

Figure 2A:
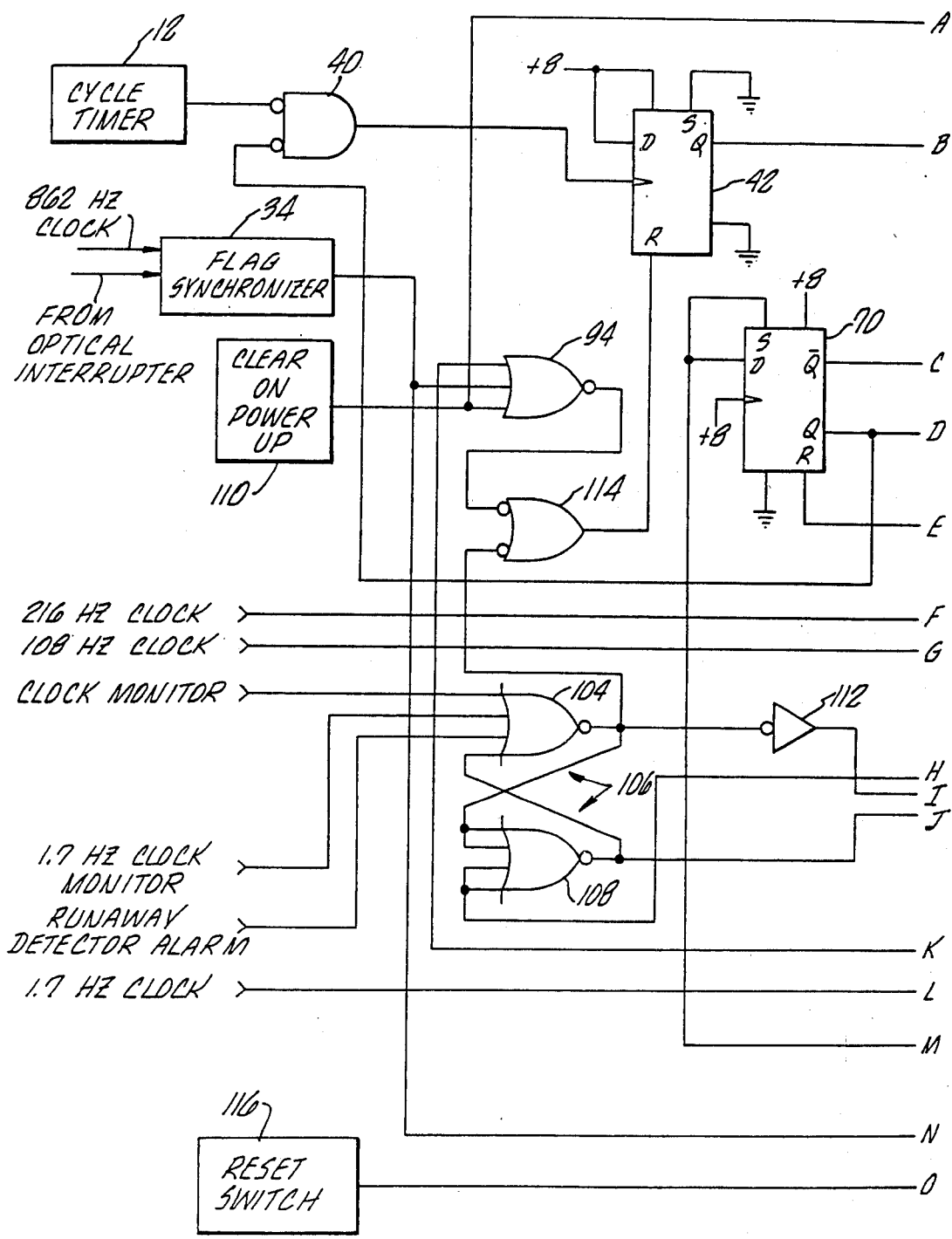

With reference now to FIG. 1, an examplary motor drive portion 10 of an infusion therapy pumping apparatus includes a cycle timer 12 which determines the frequency of the pumping cycles. The cycle timer 12 may be adjustable according to the desired infusion rate. A pumping cycle control 14 when activated by the cycle timer 12, provides a pumping cycle command signal to a motor control sequencer 16. When enabled by the pumping cycle control 14, the motor control sequencer 16 provides a plurality of sequencing signals to a stepping motor 18. The motor control sequencer 16 also controls a motor torque controller 20 and in turn a voltage regulator 22 to increase the voltage applied to the stepping motor 18 during the first predetermined portion of a normal pumping cycle. A shaft 19 of the stepping motor 18 operates a pump mechanism 24 which pumps liquid from a fluid reservoir 26 to a patient via a suitable fluid delivery system 28. The fluid reservoir 26 and the fluid delivery system 28 are generally external to the infusion therapy pumping apparatus. In the exemplary embodiment of FIG. 1, the pump mechanism 24 provides a predetermined volume of liquid to the patient through the fluid delivery system 28 for each pumping cycle.

The shaft 19 of the stepping motor 18 also carries a flag 30 which passes through an optical interrupter 32 to thereby indicate a predetermined position of the stepping motor shaft which, for example, may correspond to the position of the stepping motor shaft at the end of a complete pumping cycle. In an exemplary embodiment the flag 30 passes into the optical path of the optical interrupter 32 for each revolution of the stepping motor shaft which in turn constitutes one pumping cycle, thereby providing an indication that the stepping motor 18 is at a predetermined point in the pumping cycle.

In response to the presence of the flag 30, the optical interrupter 32 provides an output to a flag synchronizer 34 which in turn provides outputs to an occlusion detector 36 and to the pumping cycle control 14. The pumping cycle control 14 also provides an input to the occlusion detector 36. The occlusion detector 36 consequently provides outputs to the pumping cycle control 14, to the motor control sequencer 16 and also generates an occlusion alarm.

The operation of the motor drive portion 10 of FIG. 1 is initiated with the cycle timer 12 which sets the pumping cycle control 14. The pumping cycle control 14 enables the motor control sequencer 16 and also begins the operation of the occlusion detector 36 as is described below. The motor control sequencer 16 thereupon provides control signals to the stepping motor 18 and also through the motor torque controller 20 and the voltage regulator 22, increasing the voltage applied to the stepping motor 18 for a predetermined period of time at the beginning of the pumping cycle. This increased voltage consequently increases the torque generated by the stepping motor to thereby provide reliable starting of the stepping motor 18. At the end of the predetermined period, the motor torque controller 20 and the voltage regulator 22 thereupon reduce the voltage applied to the stepping motor 18 to a second predetermined running level to thus reduce the torque on the shaft 19 of the stepping motor 18 to a second predetermined running level. The stepping motor shaft 19 carries the flag 30 and operates the pump mechanism 24 through a pumping cycle to deliver a predetermined volume of liquid to the patient through the fluid delivery system 28.

If the second running torque provided by the stepping motor 18 is sufficient to overcome the pressure within the fluid delivery system 28, the flag 30 completes its revolution and passes into the optical interruptor 32. The output from the optical interruptor 32 is applied through the flag synchronizer 34 to reset the pumping cycle control 14 and the occlusion detector 36. When reset, the pumping cycle control 14 disables the motor control sequencer 16, thereby terminating rotation of the shaft 19, the flag 30 and the operation of the pump mechanism 24. This represents a completed pumping cycle.

If the second running torque developed by the stepping motor 18 continues to be sufficient to overcome the pressure within the fluid delivery system 28 for each subsequent cycle, the motor drive porition 10 continues to operate as just described for each pumping cycle command signal from the cycle timer 12.

However, if the fluid delivery system 28 is fully or partially occluded such that the pressure within the fluid delivery system 28 requires greater torque to the pump mechanism 24 than the stepping motor 18 provides, the stepping motor 18 stalls. It is then seen that the flag 30 does not complete its revolution as described above. In response to the output from the pumping cycle control 14 at the beginning of the pumping cycle, the occlusion detector 36 begins to operate substantially as a timer. If the output from the flag synchronizer 34 is not received during a first period of time which in the embodiment of FIG. 1 is approximately three times the time period required by the stepping motor 18 to complete a normal pumping cycle, that is, a pumping cycle not interrupted by stalling the stepping motor 18, the occlusion detector 36 generates an occlusion alarm output and also controls the motor control sequencer 16 so as to vary the control signals applied to the stepping motor 18 such that the torque developed by the stepping motor 18 is substantially increased. This increased torque may then allow the stepping motor 18 to complete the pumping cycle with the flage 30, the optical interrupter 32 and the flag synchronizer 34 operating as previously described. However, the occlusion detector 36 disables the motor control sequencer 16 until the occlusion detector 36 is reset as, for example, through the intervention of the pumping apparatus operator.

If, however, the increased torque provided to the stalled stepping motor 18 still does not enable the stepping motor 18 to complete the pumping cycle, then the occlusion detector 36 receives no output from the flag synchronizer 34 and, after a second predetermined period following the signal from the pumping cycle control 14, the occlusion detector 36 resets the pumping cycle control 14 to disable the motor control sequencer 16. The occlusion detector detector 36 then prevents further pumping cycle command signals from setting the pumping cycle control 14 and thereby prevents further operation of the pump mechanism 24 until the occlusion detector 36 is reset.

Thus, it is seen that the motor drive portion 10 employing the occlusion detection apparatus and method of the present invention advantageously provides relatively high stepping motor starting torque and subsequent lower stepping motor running torque. In this way, a motor drive portion 10 in accordance with the present invention provides reliable motor starting torque yet allows the stepping motor to be operated at a relatively low running torque to consequently detect relatively low occlusion pressures within the fluid delivery system. This second relatively low running torque is advantageously substantially less than the torque provided by a stepping motor that must be started and run at the same torque, therefore allowing considerably lower pressures in the fluid delivery system to be sensed.

Turning now generally to FIG. 2 wherein commonly connected lines are identified with common reference letters, the pumping cycle command signal from the cycle timer 12 is applied to a first input of an invert AND gate 40, the output of which is applied to the clock input of a D-type flip-flop 42. The Q output from the flip-flop 42 is applied to the D input of a shift register 44 and to the D input of a second shift register 46. The D input of the flip-flop 42 is connected to a high-level signal. The Q0 output of the shift register 44 is applied to both inputs of a NOR gate 48, to one input of a second NOR gate 50, and to one input each of two NAND gates 52 and 54. The Q2 output of the shift register 44 is applied to the second input of the NOR gate 50. The Q3 output of the shift-register 44 is applied to two inputs of an invert AND gate 56. The output of the gate 48 is applied to the remaining input of the gate 56. The output of the gate 56 is applied through a resistor 58 to the base of a switching transistor 60. The output of the gate 50 is applied to one input of each of four invert AND gates 62–68 and is also applied to one input of a NAND gate 71.

The Q output of a D-type flip-flop 70 is applied to a second input of a gate 54 and to the remaining input of the gate 40 while the Q-not output of the flip-flop 70 is applied to a second input of the gate 52. A 216 Hz clock signal is applied to the remaining input of the gate 52 and is also inverted via an inverter 72 to provide the clock input for the shift register 44. The 108 Hz clock signal is applied to the clock input of a D-type flip-flop 74 which is connected in a well-known fashion to divide the 108 Hz clock by two to provide a 54 Hz clock to the remaining input of the gate 54.

The outputs from the gates 52 and 54 are gated via an invert OR gate 76 to the clock inputs of two D-type flip-flips 78 and 80. The flip-flops 78 and 80 are interconnected in a suitable fashion to act as a phasing counter 77 which provides four outputs via lines 82–88 to the remaining inputs of the gate 62–68 respectively. These gates are in turn applied through an emitter-follower amplifier combination 90 such as a type 75491 and a transistor amplifier combination 92 such as a type CA3724 to the stepping motor 18. The shaft 19 of the stepping motor operates the flag 30 which passes through the interrupter beam of the optical interrupter 32 as described above and also operates the pumping mechanism (not shown).

The output of the optical interrupter 32 is applied through the flag synchronizer 34 to one input of a NOR gate 94 and to one input of a NAND gate 96. The flag synchronizer 34 synchronizes the output from the optical interrupter 32 with a 862 Hz clock from which may be derived the remaining clocks to thereby maintain synchronization of the digital logic shown in FIG. 2.

Returning to the shift register 46, the Q1 output thereof is applied to the D and to the S inputs of the flip-flop 70. Also, the Q3 output of the register 46 is applied to one input of NOR gate 98 and to one input of the gate 94. The remaining input of the gate 98 is responsive to 1.7 Hz clock and the output thereof is connected to the clock input of the register 46.

The Q-not output of the flip-flop 70 is connected to a second input of the gate 96. The outputs of the gates 96 and 70 are applied to an invert OR gate 100, the output of which is applied to reset input of the shift register 46. The output of the gate 71 is also applied through an inverter 102 to the reset input of the flip-flop 70.

A first NOR gate 104 of a malfunction latch 106 receives inputs from a clock monitor, a 1.7 Hz clock monitor, a runaway detector alarm and from the output of a second NOR gate 108. The gate 108 similarly receives an input from the output of gate 104. A clear on power up generator 110 provides a pulse to the remaining inputs of the gate 108 when power is applied to the infusion pumping apparatus. The clear on power up generator 110 also provides a clear pulse to the reset input of the shift register 44 and to the reset (R) inputs of the flip-flops 74, 78 and 80. The output of the gate 104 is applied through an inverter 112 to provide a malfunction output and is also applied to one input of an invert OR gate 114. The output of the gate 108 is also applied to the set (S) input of the flip-flops 78 and 80.

With reference again to gate 94, the output thereof is applied to the second input of the gate 114, the output of which is applied to the reset (R) input of the flip-flop 42.

A reset switch 116, when accuated by the operator of the infusion pumping apparatus, provides a reset pulse to the second input of the gate 71.

The voltage regulator 22 generally comprises an intergrated circuit regulator 118 driving a PASS transistor 12 in a conventional fashion. The transistor 60, operating through a resistor 122 shunts a resistive feedback network 124 which provides voltage feedback to the regulator 118. Power for the transistor 120 is applied via a line 124 while control power for the regulator 118 is applied via a line 126. The output of the regulator 118 is applied to the stepping motor 18.

In operation, the clear on power up generator 110 provides an output pulse when power is applied to the infusion pumping apparatus. This pulse is applied through the gates 94 and 114 to reset the flip-flop 42 and also resets the shift register 44 and the flip-flops 74, 78, and 80. The output from the clear on power up generator 110 is also applied to the malfunction latch 106 to clear the latch and thereby remove a set input applied to the flip-flops 78 and 80 via the gate 108. A high-level output at the gate 104 is inverted by the inverter 112 to remove a malfunction output signal. To further initialize the apparatus, the reset switch 116 is operated, resetting the shift register 46 through the gates 71 and 100 and also resetting the flip-flop 70 through the gate 71 and the inverter 102.

To begin the pumping cycle, cycle timer 12 provides a pumping cycle command pulse to the gate 40. With the flip-flop 70 reset, the pulse from the cycle timer 12 is applied through the gate 40 to the clock input of the flip-flop 42 which in turn is set, generating a high-level Q output. The gate 40 and the flip-flop 42 may be generally considered to comprise the pumping cycle control 14 of FIG. 1.

The output of the flip-flop 42 (FIG. 2) as applied to the shift register 44, enables the shift register 44 to propogate the inverted 216 Hz clock that is applied thereto. With the first such clock pulse, the Q0 output of the shift register 44 provides an output through the gate 48 to the gate 56 the gate 48 operating as an inverter. Thus, the low-level output from the gate 48 and the low-level output from the Q3 output of the shift register 44 produces a high-level signal at the output of the gate 56 which is applied through the resistor 58 to the transistor 60. This signal switches the transistor 60 into a conducting state, thus shunting the resistive network 124 which provides feedback to the regulator 118. Consequently, the output of the regulator 118 increases to thereby increase the voltage applied to the stepping motor 18.

Returning to the shift register 44, the Q0 output is also applied to the gate 50 and in response thereto, the output of the gate 50 becomes a low-level signal which enables the gates 62–68. The output of gate 50 is also applied to the gate 71 to prevent a reset signal from being applied therethrough to the shift register 46 and the flip-flop 70.

The Q0 output from the shift register 44 is further applied to the gates 52 and 54. With the flip-flop 70 reset, the Q-not output of the flip-flop 70 enables the gate 52 to apply 216 Hz clock pulses through the gate 76 to the phasing counter 77. It is noted that the low-level output at the Q terminal of the flip-flop 70 prevents 54 Hz clock pulses from being applied through the gate 54. In response to the 216 Hz clock pulses from the gate 76, the phasing counter 77 provides suitably sequenced signals on the lines 82–88 which are in turn applied through the gates 62–68, the emitter-follower amplifier combination 90, and the transistor amplifier combination 92, thereby allowing current to flow through the stepping motor 118. In response thereto, the shaft 19 of the motor 18 is rotated initially at a relatively high first torque to thereby operate the pump mechanism 24 as seen in FIG. 1. It is also to be noted that the flag 30 is rotated by the shaft 19.

As the inverted 216 Hz clock pulses are applied to the shift register 44, the register 44 propagates the high-level input sequentially to the remaining outputs Q1–Q3 respectively. As this propagation progresses, a high-level Q2 output produces a continued low-level output from the gate 50.

However, when the Q3 output transitions to a high-level, the gate 56 thereupon produces a low-level output which causes the transistor 60 to switch to a non-conductive state. In this instance, the regulator 22 then provides a lower voltage regulated output to the stepping motor 18 and thus decreases the stepping motor torque to a second predetermined level. It is seen that by adjusting a potentiometer which is a portion of the resistive network 124, the second and lower torque produced by the stepping motor may be easily and accurately adjusted to thereby adjust the pressure within the fluid delivery system 28 at which the stepping motor 18 stalls. Thus, the shift register 44, the gates 48 and 56, and the transistor 60 adjusts the voltage applied to the stepping motor 18 to provide an initial high starting torque for approximately three cycles of the inverted 216 Hz clock and then adjusts the stepping motor operating voltage to then provide a lower second running torque from the motor for the remainder of a normal pumping cycle. In a preferred embodiment, approximately 48 cycles of the 216 Hz clock provide outputs from the phasing counter 77 which cause the stepping motor shaft 19 to complete one revolution, that is, one pumping cycle. Therefore, approximatley three cycles of the inverted 216 Hz clock represents a relatively small portion of a pumping cycle.

Generally, the shift register 46 and the flip-flop 70 provide the occlusion detection function performed by the occlusion detector 36 of FIG. 1. As noted previously, the output from the flip-flop 42 (FIG. 2) is applied to the D input of the shift register 46. Consequently, this input may be propagated through the shift register 46 by 1.7 Hz clocks applied via the gate 98. At least two such clock pulses must be received by the shift register 46 before the Q1 output changes state (Q0 output not shown). As described previously, approximately 48 cycles of the 216 Hz clock are required to operate the stepping motor 18 through a pumping cycle which is therefore approximately 0.2 seconds. Since at least two 1.7 Hz clock pulses are required to produce the high-level Q1 output from the shift register 46, it is seen that at least approximately 0.6 seconds are required before the occlusion detection shift register 46 provides a first high-level output. Consequently, if the pressure within the fluid delivery system 28 is such that the stepping motor 18 does not stall during the pumping cycle, the stepping motor shaft 19 completes one revolution and the flag 30 is detected by the optical interrupter 32. As previously noted, this complete cycle may occur in an exemplary embodiment in approximately 0.2 seconds. The output from the interrupter 32 is applied through the flag synchronizer 34 and the gates 94 and 114 to reset the flip-flop 42. The flag synchronizer also applies a signal through the gates 96 and 100 to reset the shift register 46. In this instance, the pumping cycle has been successfully completed in less than a first predetermined time period as measured by the shift register 46 and thus the register 46 provides no output indicative of an occlusion within the fluid delivery system 28.

With continued reference to FIG. 2 and, in particular, to flip-flop 42 and the shift register 44, once the flip-flop 42 is reset, the low-level Q output thereof is propagated through the shift register 44 outputs Q0–Q3 respectively in accordance with the inverted 216 Hz clock. First, with a low-level Q0 output, the gates 48 and 56 maintain a low-level signal to the transistor 60, thus maintaining the transistor 60 in a non-conducting state. Also, the Q0 output does not change the output of the gate 50 because the Q2 output of the shift register 44 remains at a high level. However, the Q0 low-level output prevents further clock pulses from being applied through the gates 52 and 54 to the phasing counter 77 and thus the stepping motor 18 no longer receives sequential signals to enable the rotation of the shaft 19.

As the low-level input to the shift register 44 propogates therethrough, the Q2 output becomes low-level, thus generating a high-level output at the gate 50 which disables the gates 62–68. It is to be noted that there is a slight delay from the time that the clock pulses are removed from the phasing counter 77 until the gates 62–68 are disabled. This advantageously allows current to continue to flow through the stepping motor 18 for a short period of time to thereby effectively brake further rotation of the shaft 19.

As the low-level input to the shift register 44 continues to be propagated therethrough, the Q3 output provides a low-level output to the gate 56. However, the output from the gate 48 maintains the output of the gate 56 at a low-level.

For each pumping cycle, the above-described operation is repeated if the pressure within the fluid delivery system 28 does not cause the stepping motor 18 to stall. Thus, with each pumping cycle, the pump mechanism 24 (FIG. 1) delivers a predetermined volume of liquid from the fluid reservoir 26 to the patient via the fluid delivery system 28.

Assuming, however, that during the pumping cycle which begins as just described the pressure within the fluid delivery system 28 causes the stepping motor 18 to stall, the following operational sequence occurs. With the stepping motor 18 in a stalled condition, the flag 30 is not detected by the optical interrupter 32 and thus no signal from the flag synchronizer 34 is provided to the gates 94 and 96 (FIG. 2). In this instance, and with the second clock pulse applied to the occlusion detection shift register 46, the Q1 output thereof applies a set signal to the flip-flop 70 which functions as an occlusion detection latch. The set signal changes the output state of the flip-flop 70 and, consequently, 54 Hz clock is selected by the gate 54 and applied through the gate 76 to the phasing counter 77. The phasing counter 77 then generates lower frequency sequential signals on the lines 82–88. Because the windings within the stepping motor 18 are primarily inductive in nature, the decreased frequency allows the current within those windings to increase, thereby increasing substantially the torque generated by the motor 18 and applied via the shaft 19 to the pump mechanism 24. This increased torque may overcome the pressure within the fluid delivery system 28 to thereby complete the pumping cycle as described above. However, the Q-not output of the flip-flop 70 inhibits the gate 96 and thus the occlusion detection shift register 46 is not reset from the output of the flag synchronizer 34. Also, the flip-flop 70 Q output applied to the gate 40 prohibits further pumping cycle command pulses from the cycle timer 12 from clocking the flip-flop 42 and thus inhibits further pumping cycles. With reference to shift register 46, the high-level signal that is propagated to the Q1 output thereof continues to propagate through the shift register 46 in response to the 1.7 Hz clock until the Q3 output becomes a high-level, thereby inhibiting further clocking of the shift register 46 throught the gate 98.

In order to reset the motor drive portion 10, the reset switch 116 (FIG. 2) must be operated to thereby reset the shift register 46 and the occlusion detection latch flip-flop 70. It is to be noted that the reset signal may only be applied to the shift register 46 and the flip-flop 70 through the gate 71 when the output of the gate 50 is a high-level signal, indicating that the pumping cycle has been completed as described above.

As just described, the shift register 46 and the flip-flop 70 control the gates 52 and 54 and thus the phasing counter 77 to increase the torque provided by the stepping motor 18 once an occlusion is detected. If, however, the increased torque is not sufficient to complete the pumping cycle, then the high-level signal propagated through the shift register 46 appears at the Q3 output thereof and resets the flip-flop 42 through the gates 94 and 114. The shift register 44 and the associated circuitry then operate as previously described to de-energize the stepping motor 18.

The malfunction latch 106 is responsive to various malfunction detection signals as described above, and if a malfunction is detected, the output of the gate 104 resets the flip-flop 42 through the gate 114 to terminate the pumping cycle. The gate 104 and the inverter 112 cooperate to provide a malfunction output indicative of a malfunction state. Also, the gate 108 provides a set (S) input to the flip-flops 78 and 80 of the phasing counter 77 to prohibit further sequential signals from being applied to the stepping motor 18.

In an exemplary embodiment, the D-type flip-flops may be a type 4013 and the shift registers 44 and 46 may be a type 4015.

It will be apparent to those skilled in the art that the improved occlusion detection method and apparatus of the present invention can be implemented using other suitable means such as, for example, a micro-processor or micro-computer. Moreover, logic circuitry other than the exemplary embodiment disclosed herein may be suitably employed.

Thus, the occlusion detection method and apparatus of the present invention provides a first starting torque from a stepping motor 18 to provide reliable starting thereof, yet the stepping motor is operated throughout the remainder of a normal pumping cycle at a substantially lower torque to thereby accurately detect increased pressure and thus occlusion within the fluid delivery system. Moreover, an apparatus and method in accordance with the present invention is relatively simple, easily implemented, and reliable while allowing the stepping motor stall torque and the consequential pressure within the fluid delivery system to be easily adjusted and to be set to relatively low levels.

Having thus described one embodiment of my invention in detail, it is to be understood that numerous equivalents and alternatives which do not depart from the invention will be apparent to those skilled in the art, given the teachings herein. Thus, my invention is not to be limited to the above description but is to be of the full scope of the appended claims.

What is claimed is:

1. An occlusion detection apparatus for use in a pumping apparatus wherein said pumping apparatus includes a motor for accuating pumping means through a pumping cycle to provide pumping of a fluid through fluid delivery means, comprising first means for energizing the motor to operate the motor at a first torque for a predetermined time period at the beginning of the pumping cycle and for subsequently operating the motor at a second torque less than the first torque, and second means for determining if the pumping cycle is not completed within a second predetermined time period to thereby indicate an occlusion within the fluid delivery means.

2. An occlusion detection apparatus as in claim 1 wherein the predetermined time period of the first means is substantially less than the time required for the motor to complete the pumping cycle.

3. An occlusion detection apparatus as in claim 1 wherein the second means is additionally for controlling the first means to de-energize the motor if the pumping cycle is not completed within a third predetermined time period.

4. An apparatus as in claim 3 wherein the first means is further responsive to the second means for subsequently operating the motor at a third torque greater than the second torque if the pumping cycle is not completed within the second predetermined time period.

5. An occlusion detection apparatus for use in a pumping apparatus, wherein said pumping apparatus includes a motor for actuating pumping means through a pumping cycle to provide pumping of a fluid through fluid delivery means, comprising first means for energizing the motor to operate the motor at a first torque for a first predetermined time period at the beginning of the pumping cycle and for subsequently operating the motor at a second torque less than the first torque, the first predetermined time period being substantially less than the time required for the motor to complete the pumping cycle, second means for providing an output when the motor is in a predetermined portion of the pumping cycle, third means responsive to the second means for providing an indication of an occlusion within the fluid delivery means if the output from the second means is not provided within a second predetermined time period after the beginning of the pumping cycle.

6. An occlusion detection apparatus as in claim 5 wherein said first means is additionally for providing a first potential to the motor to operate the motor at the first torque and for providing a second potential to the motor to operate the motor at the second torque.

7. An occlusion detection apparatus as in claim 6 wherein the third means is additionally for controlling the first means to de-energize the motor if the output from the second means is not provided within a third predetermined time period.

8. An apparatus as in claim 7 wherein the first means is further responsive to the indication of the third means for subsequently operating the motor at a third torque greater than the second torque.

9. An occlusion detection apparatus for use in a pumping apparatus wherein said pumping apparatus includes a stepping motor for actuating pumping means to provide intermittent pumping of a fluid through fluid delivery means, comprising first means for providing control signals to the stepping motor in response to a pumping cycle signal, the control signals being adapted to step the motor shaft, second means for providing a first potential to the motor to operate the motor at a first torque for a predetermined time after receipt of the pumping cycle signal and for subsequently providing a second potential to the motor to operate the motor at a second torque less than the first torque, third means for providing an output when the motor shaft is in a predetermined position, and fourth means responsive to the pumping cycle signal for providing an output indication of an occlusion within the fluid delivery means if the output from the third means is not provided within a predetermined time period after the pumping cycle signal.

10. A method for detecting occlusions in fluid delivery means of a pumping apparatus wherein the pumping apparatus includes a motor for actuating pumping means through a pumping cycle to provide pumping of a fluid through the fluid delivery means, comprising the steps of operating the motor at a first torque during a first portion of the pumping cycle, operating the motor at a second torque less than the first torque during a subsequent portion of the pumping cycle, and determining if the pumping cycle exceeds a first predetermined time period to thereby indicate an occlusion within the fluid delivery system.

11. A method as in claim 10 wherein the time period of the first portion of the pumping cycle is substantially less than the time required for the motor to complete the pumping cycle.

12. A method as in claim 10 including the additional step of de-energizing the motor if the pumping cycle exceeds a second predetermined time period.

13. A method as in claim 10 wherein the method includes the additional step of operating the motor at a third torque greater than the second torque if the pumping cycle exceeds the first predetermined time period.

14. A method for detecting occlusions in fluid delivery means of a pumping apparatus wherein said pumping apparatus includes a motor for actuating pumping means through a pumping cycle in response to a pumping cycle command to provide intermittent pumping of a fluid through fluid delivery means, comprising the steps of providing control signals to the motor in response to a pumping cycle command, the control signals being adapted to control the rotation of the motor shaft, operating the motor at a first torque for a first predetermined time period after the the pumping cycle command, the predetermined time period being substantially less than the time required for the motor to complete the pumping cycle, operating the motor at a second torque less than the first torque after the first predetermined time period, determining when the motor shaft is in a predetermined position, and providing an output indicative of an occlusion within the fluid delivery means if the motor shaft has not achieved the predetermined position within a second predetermined time period after the pumping cycle command.

15. A method as in claim 14 wherein the first operating step includes providing a first potential to the motor and the second operating step includes providing a second potential to the motor.

* * * * *